United States Patent
Frischauf et al.

(10) Patent No.: US 7,338,802 B2
(45) Date of Patent: Mar. 4, 2008

(54) METHOD OF PERFORMING CALIBRATION AND QUALITY CONTROL OF A SENSOR AND APPARATUS FOR PERFORMING THE METHOD

(75) Inventors: Peter Aage Frischauf, Brøndby (DK); Eiler Larsen, Brøndby (DK)

(73) Assignee: Radiometer Medical ApS, Brønshøj (DK)

( * ) Notice: Subject to any disclaimer, the term of this patent is extended or adjusted under 35 U.S.C. 154(b) by 909 days.

(21) Appl. No.: 10/695,646

(22) Filed: Oct. 29, 2003

(65) Prior Publication Data

US 2004/0132193 A1 Jul. 8, 2004

Related U.S. Application Data

(60) Provisional application No. 60/479,729, filed on Jun. 20, 2003.

(30) Foreign Application Priority Data

Oct. 30, 2002 (DK) .............................. 2002 01647

(51) Int. Cl.
*G01N 33/00* (2006.01)
(52) U.S. Cl. .............................. 436/8; 436/43; 436/63; 422/67; 422/68.1; 73/1.01; 73/1.02; 73/1.03
(58) Field of Classification Search ............... 436/8, 436/11–16, 43, 50, 63, 68; 422/67, 68.1, 422/73; 73/1.01, 1.02, 1.03
See application file for complete search history.

(56) References Cited

U.S. PATENT DOCUMENTS

| 4,163,734 | A |   | 8/1979  | Sorensen et al. |
|-----------|---|---|---------|-----------------|
| 4,469,792 | A |   | 9/1984  | Simmonds et al. |
| 4,701,417 | A |   | 10/1987 | Portenhauser et al. |
| 4,786,394 | A |   | 11/1988 | Enzer et al. |
| 4,871,439 | A |   | 10/1989 | Enzer et al. |
| 5,422,278 | A |   | 6/1995  | Herring |
| 5,518,929 | A |   | 5/1996  | Herring |
| 5,750,906 | A |   | 5/1998  | Parker et al. |
| 5,910,445 | A |   | 6/1999  | Larsen |
| 5,976,085 | A | * | 11/1999 | Kimball et al. ............ 600/309 |
| 6,037,178 | A |   | 3/2000  | Leiner et al. |
| 6,171,865 | B1|   | 1/2001  | Weigl et al. |

FOREIGN PATENT DOCUMENTS

DE 41 04 302 A1 8/1992
WO WO 02/066973 A 8/2002

* cited by examiner

*Primary Examiner*—Maureen M. Wallenhorst
(74) *Attorney, Agent, or Firm*—Morgan, Lewis & Bockius LLP

(57) ABSTRACT

A method of performing calibration and quality control of a sensor for determining a parameter in a test fluid in which method a calibration and quality control cycle is repeated. A cycle includes the steps of performing a calibration and a quality control of the sensor using independent reference materials. In the method a reference material is in one cycle used in the quality control step which in a previous cycle was used in the calibration step. The present invention further provides an apparatus for performing the method.

35 Claims, 2 Drawing Sheets

METHOD OF PERFORMING CALIBRATION AND QUALITY CONTROL OF A SENSOR AND APPARATUS FOR PERFORMING THE METHOD

This application claims the benefit of U.S. provisional application No. 60/479,729 that was filed on Jun. 20, 2003, which is hereby incorporated by reference.

BACKGROUND OF THE INVENTION

1. Field of the Invention

The present invention relates to a method of performing calibration and quality control of a sensor for determining a parameter in a test fluid as well as an apparatus for performing the method.

2. Discussion of the Related Art

Sensors for measuring a parameter in a test fluid are widely used in various fields of industries. Examples of industries are the food industry, the environmental industry and the medical and the clinical industry, in particular the clinical laboratory industry.

In order to assure that sensor measurements are accurate it is required to regularly calibrate the sensors, i.e. to determine experimentally the correspondence between sensor responses and predetermined parameter values of the reference materials, usually by measurements on one or more reference materials.

In many cases it is also required to regularly control the quality of the sensor performance, i.e. to verify experimentally that the sensor measurements are accurate and/or precise, usually by comparison of a measured parameter value of a reference material with an acceptance range of the same reference material.

In the food industry such routines of calibration and quality control are performed for instance on sensors for assessing milk quality. In the medical and clinical industry such calibration and quality control routines are performed for instance on sensors for determining parameters in physiological fluids.

DE 41 04 302 discloses a method of performing quality control and optionally calibrating a sensor for determining a parameter in a physiological fluid. According to the method, the same volume of reference solution may be used to control and, if needed, to calibrate a measuring cell. The advantage is that the same reference solution may be used both in measuring cells for determining the hematocrit value and in cells for determining physiological electrolytes. In the method, however, the same volume of reference solution is used for both calibration and quality control of the sensor, and therefore the method does not provide for an independent assessment of sensor performance.

The general requirement for reference materials for performing calibration and quality control routines is, that the reference material used in quality control of a sensor must be different from the reference material(s) used for the calibration upon which the quality control is based in order to ensure that the quality control procedure provides an independent assessment of sensor performance.

In the clinical and medical industry, legislation requires that sensors are exposed to quality control procedures in addition to regular calibration procedures. The quality control procedures must be performed often enough and covering a broad enough parameter range to be able to prove, at any time, that the sensor used is able to provide reliable data in its entire measuring range. This means that sensors must be checked by means of a system, which is independent of the normal calibration system of the sensor.

It is accordingly recommended that in successive quality control cycles the quality of a sensor is controlled using a number of reference materials representing different parameter levels (often low, middle and high).

The same reference material may represent several different parameters at a time. This way calibration and/or quality control may be performed on several sensors simultaneously using only one reference material. One level of one parameter may be combined with any level of other parameters. An example of such a reference material is found in U.S. Pat. No. 5,910,445 disclosing quality control liquids for use in the quality control procedure of electrochemical measuring apparatuses for measurement on physiological liquids.

Further, U.S. Pat. No. 4,701,417 discloses calibration and control sera for use in lipid diagnosis. Solutions for calibrating and/or quality controlling sensors in blood gas analysers are disclosed in, for example, U.S. Pat. Nos. 5,422,278 and 5,910,445. In all cases the reference materials for calibration and the materials for quality control are described as two separate groups of reference materials.

In automatic apparatuses for blood gas analysis it is standard procedure to use at least five different reference materials in the calibration and quality control of the respective sensors. An example is the blood analyser ABL™725 manufactured by Radiometer Medical A/S. In this apparatus several different blood parameters are determined. It contains two calibration solution containers which are integrated in the apparatus and which need to be renewed approximately once a month.

In the ABL™725 blood analyser, the quality control may be performed manually by a specially trained operator at specific hours by aspirating reference solution from an ampoule. After shaking and breaking open the ampoule, it is provided with an adapter for attaching it to the inlet upon which an automated quality control procedure is initiated. When the operator has obtained a measuring result, he or she must determine whether the result falls within a certain acceptance range, which is given on an insert of the ampoule. It is recommended that reference materials of at least three different parameter levels are used.

Alternatively, the ABL™725 blood analyser may be provided with a module (AutoCheck™) for automatic aspiration of control fluid from an ampoule for quality control of the apparatus. With this module, operator handling is reduced to removing a holder from the apparatus, loading the holder with ampoules and reinserting it. This must be done approximately once a week. The operator still needs to pay attention to the number of ampoules of each level that he or she loads into the holder.

Thus, in the known methods of performing calibration and quality control of a sensor for determining a parameter in a test fluid, a substantive number of different reference materials are required. Also, the known methods require that a specially trained operator perform the quality control routine or at least once a week load a holder with ampoules for automatic aspiration of quality control fluid.

SUMMARY OF THE INVENTION

One object of the invention is to provide a method of performing calibration and quality control of a sensor for determining a parameter in a test fluid in which method the number of reference materials may be reduced yet retaining the same precision and accuracy in the calibration and quality control of the sensor and yet fulfilling the requirement that the reference material used in the quality control is different from the reference material(s) used in the calibration upon which the quality control is based.

Another object of the invention is to provide an apparatus for determining a parameter in a test fluid in which the apparatus employs the method according to the invention for performing calibration and quality control of a sensor contained in the apparatus.

A further object of the invention is to provide a method and an apparatus which allow automated handling of the quality control procedure of a sensor. Thus the required maintenance and the need for specially trained operators for operating such apparatuses is minimised. Moreover, the risk of human error is minimised as well.

Additional objects and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

The object is achieved by providing a method of performing calibration and quality control of a sensor for determining a parameter in a test fluid in which a calibration and quality control cycle is repeated, where the cycle includes: performing at least one calibration of the sensor using a reference material representing a parameter level of the parameter; performing at least one quality control of the sensor, as calibrated, using another reference material representing another parameter level of the parameter than in the calibration step, and repeating the above steps for at least two cycles, wherein in one cycle the reference material used in the quality control step was used in the calibration step of a previous cycle.

One embodiment of the present invention has the advantage that the number of reference materials can be reduced by using the same reference materials both for calibration and for quality control purposes without reducing the quality of the calibration and the quality control and yet retaining the independence between the calibration system and the quality control system. The only requirement is that the same reference material is not used both in the quality control step and in the calibration step upon which the quality control is based.

A reduction in the number of reference materials makes it possible to reduce the storage space for reference material. If this space is inside an apparatus provided with the sensor, the size of the apparatus may be reduced.

The fully automated handling of the quality control procedure of a sensor has the advantage that the requirement of specially trained operators for operating such apparatuses as well as the risk of human errors are minimised.

The test fluid to be analysed may be any fluid in which it is desired to determine a parameter. Examples are fluids in food processing, such as beer, milk and meat processing fluids, and physiological fluids, such as whole blood, blood plasma, serum, cerebrospinal fluids, spit and urine.

The parameter towards which the sensor may be specific may be any parameter of interest, for example:

viscosity, density, pressure, conductivity, and surface tension.

Of particular interest are parameters of physiological fluids such as pH, concentrations of electrolytes, such as $Li^+$, $Na^+$, $K^+$, $Ca^{2+}$, $Mg^{2+}$, $Cl^-$, $HCO_3^-$ and $NH_3$ ($NH_4^+$), concentrations of dissolved gases, notably oxygen and carbon dioxide (conventionally reported in the form of partial pressures, e.g. $pO_2$, $pCO_2$), hematocrit (Hct), concentration of haemoglobin and haemoglobin derivatives, such as oxyhaemoglobin, deoxyhaemoglobin, methaemoglobin, carboxyhaemoglobin, sulfhaemoglobin and fetal haemoglobin, concentrations of metabolic factors, such as glucose, creatinine, creatine, urea (BUN), uric acid, lactic acid, pyruvic acid, ascorbic acid, phosphate, protein, bilirubin, cholesterol, triglycerides, phenylalanine and tyrosine, concentrations of enzymes, such as lactic acid dehydrogenase (LDH), lipase, amylase, choline esterase, alkaline phosphatase, acid phosphatase, alanine amino transferase (ALAT), aspartate amino transferase (ASAT) and creatinine kinase (CK), and concentrations of ligands, such as antibodies and nucleotide fragments.

A sensor may include any kind of device of which some part, in the present context called the sensing part, is capable either of selectively interacting with the chemical species of interest, thereby producing a well-defined and measurable response which is a function of the desired characteristic of that chemical species, the desired characteristic thus being derivable therefrom, or of responding to a bulk property of a fluid, the response not being selective with respect to any specific chemical species, but being a function of the total concentration of one or more chemical species in the liquid, the desired characteristic thus being derivable therefrom.

Relevant types of sensors are those adapted to determine any of the previously mentioned parameters, for example:

potentiometric sensors for use in aqueous media, such as ion-selective electrodes for specific measurement of the concentration of selected ionic chemical species, the response being in the form of an electric potential, amperometric sensors, such as sensors for the determination of oxygen partial pressure, whose response is in the form of an electric current, optical sensors, such as sensors producing a colour response to a particular chemical species, the response being measured spectrometrically using reflectance or transmittance, and the colour response being a colour intensity or the decay of colour intensity, piezoelectric sensors, thermometric sensors, pressure-change sensors, acoustic sensors, enzyme-based sensors employing an enzymatic reaction and generating a response on the basis of any relevant physical principle, for example any of those principles employed in the sensor types listed above; examples are enzyme-based thermistors and enzyme-based amperometric sensors for use in the measurement of concentrations of metabolic products, e.g. glucose, urea, creatinine or lactate, and affinity sensors comprising one moiety of an affinity pair, e.g. an antigen/antibody pair or two complementary nucleotide fragments, the other moiety being the chemical species of interest.

The sensor may be of any design. Accordingly, both miniaturized, planar sensors and conventional sensors are suitably calibrated and quality controlled by the method according to an aspect of the present invention.

Sensors generally perform a conversion function to convert the energy form associated with the change occurring at the surface of the sensing part to electrical energy or electromagnetic radiant energy, the sensor response thereby being registerable in the form of an electrical or optical signal.

The measured sensor response may be a one-point measurement, an average of a slightly varying signal, a transient or an estimate based on a transient. It may be preferable to obtain several responses and use an average of these.

The calibration of the sensor includes the experimental determination of the correspondence between the sensor responses and predetermined parameter values of a reference material. Usually, the correspondence is found by obtaining sensor responses to one or more reference materials having predetermined parameter values and determining the correspondence between those.

The correspondence is most often expressed as a regression function calculated from the predetermined parameter values and the corresponding sensor responses. Alternatively, if the measuring results are shown directly on a graduated scale, the graduated scale may be moved to show the predetermined parameter value of the reference material.

The correspondence determined in the above calibration is then used when a parameter in a test fluid is to be determined. First a sensor response to the test fluid is obtained. Then the sensor response is converted into a measured parameter value by using the correspondence determined.

The conversion may be effected by programmed control means comprising an algorithm to provide a measured parameter value. The algorithm is adjusted in each calibration step.

Any number of reference materials may be used in the calibration step. The number of reference materials which are required to obtain a reliable calibration of a sensor depend on the nature of the sensor and of the demands for accuracy and/or precision. It is thus preferred to use reference materials representing one to five different parameter levels in the calibration step. Two or three different levels is more preferred in many instances, since this for most sensors provides a sufficiently reliable result and at the same time limits the number of different reference materials. For some sensors, e.g. many biosensors, it is however required to use four or five reference materials to obtain sufficiently reliable results.

It may be sufficient to initially calibrate the sensor once using more than one reference material. Any subsequent calibrations may then be performed using only one reference material and is simply used to correct the previously determined correspondence between sensor responses and predetermined parameter values.

However many sensors need to be calibrated regularly and often using reference materials representing at least two parameter levels. A calibration using reference materials representing more than two parameter levels may in some cases provide a more reliable calibration. For instance, oximetry modules are often calibrated in one point, many ion selective sensors in two points, and many enzyme sensors in three points.

One of the reference materials used in the calibration of the sensor may be a blank. That is, it may represent a parameter level of "zero".

The quality control of the sensor includes the experimental verification that the sensor measurements are accurate and/or precise. Usually such verification is performed by determining whether a measured parameter value of a reference material is within an acceptance range thereof. The measured parameter value of the reference material is obtained by converting the sensor response into the measured parameter value using a calibration correspondence as described above. It is then determined whether the measured parameter value is within the acceptance range of the reference material.

The acceptance range is generally centered around a predetermined parameter value. The limits of the range depend, e.g., on sensor variation, on the variation when determining the predetermined parameter value of the reference materials for both the quality control and the calibration and/or demands for accuracy and precision.

The calibration and quality control cycle includes one calibration and one quality control where the correspondence determined in the calibration is used in the cycle for converting the sensor response to the reference material of the quality control into a measured parameter value.

In the method, all reference materials may be used in each calibration and quality control cycle, or a selection among the total number of reference materials may be used in each cycle. The only demand is that the total number of reference materials at least equals the number of quality control levels desired.

There is no demand as to any time interval between the calibration and the quality control, nor to the time interval between two cycles. If it is desired to control performance of the sensor and the apparatus as well as the quality of the reference materials, the quality control should preferably be performed fairly shortly after the calibration upon which the quality control is based. If it is desired to control the drift of a sensor within a certain period of time the calibration upon which the quality control is based should preferably be performed at the beginning of the period and the quality control at the end of the period.

Between one cycle of calibration and quality control and a previous cycle of calibration and quality control supplementary calibrations and/or quality controls may be performed on the same or different reference materials.

A previous cycle denotes a cycle, which is carried out any number of cycles before the cycle in question.

The order in which the individual steps of the method are performed is not important. The only demand is that the correspondence of the calibration upon which the quality control is based must be obtained before the measured parameter value may be obtained in the quality control.

A reference material includes a material representing an exact parameter value. It is preferred that the reference material retains a constant value for an extended period of time. Reference materials for use in the same cycle must be prepared independently of each other in order to provide an independent assessment of sensor performance.

Such reference material preferably has a predetermined parameter value. This may be the experimental determination of the parameter value itself, or it may be the same adjusted to take into account various systematic errors in the measuring method. Examples of such errors affecting systematically the measured result are the nature of the test fluid and the apparatus and the sensor with which the test fluid is analysed as well as residues near the sensor surface and measurements performed before equilibrium is obtained at the sensor surface.

Since the procedure of performing the calibration may deviate from that of the quality control, one reference material may have one predetermined parameter value for use in the quality control and another predetermined parameter value for use in the calibration, the two values taking into account different systematic errors.

A reference material may be referred to as representing or having a parameter level. This level is to be understood as an approximate parameter value of a given reference material, the exact parameter value lying in the neighbourhood of the level.

The reference materials may be in fluid or solid form and contain or mimic any of the parameters mentioned earlier. If in fluid form, the reference materials are preferably provided in sealed containers.

In apparatuses designed for analysing fluids, it is preferable that the reference materials are fluids, for example a liquid, a gas or a combination thereof.

If the reference material is a fluid, the fluid may also contain constituents having a rinsing action. Thus a separate rinsing or cleaning solution may be omitted or used more rarely.

For some optical sensors the reference materials may be a solid brick or filter comprising a colour inducing material.

In a full calibration and quality control routine, the cycle is repeated until all available reference materials have been used at least once for the quality control of the sensor performance. Thus the performance of the sensor is controlled at all the different parameter levels in one routine providing a more reliable quality control of the sensor.

Preferably this routine is systematically repeated, making the method even more suitable for being automatically performed.

The correspondence determined in the above calibration step may be a first calibration for performing the quality control of the sensor. Subsequently, a second calibration may be performed in the same cycle based on the same reference materials as were used in the first calibration and the quality control. The correspondence of the second calibration may then be used when a parameter in a test fluid is to be determined.

By doing this, a second calibration is obtained which includes one more calibration point than the first one without increasing the total number of reference materials. Such calibration provides in some cases measured parameter values with less variation than the first calibration does, for instance in many blood measurements.

The second calibration may be performed in various ways. In one embodiment, a cycle comprises obtaining sensor responses to the reference materials used in the first calibration step and the quality control step, obtaining a further sensor response to the reference material used in the quality control step, and performing a second calibration based on the sensor responses obtained in the first calibration step and on the further sensor response obtained. This embodiment is preferred if the procedure of performing the quality control measurement is different from the procedure of performing the calibration measurement.

According to another embodiment the second calibration is based on the sensor responses obtained in the first calibration step and in the quality control step. Thus the step of performing the second calibration only includes performing a second calculation of the correspondence between sensor responses and predetermined parameter values not a second round of measurements.

The introduction of a step of performing a second calibration into a calibration and quality control of a sensor, even without the previously described cyclic use of the reference materials, may result in a reduction in the use of reference materials if the same reference materials are used in the second calibration as were used in the first calibration.

Accordingly the object may further be achieved by providing a method of performing calibration and quality control of a sensor for determining a parameter in a test fluid, that includes: performing a first calibration of the sensor using a reference material representing a parameter level; performing a quality control of the sensor as calibrated using a reference material representing another parameter level than in the calibration step; and performing a second calibration of the sensor using the same reference materials as were used in the steps of performing the first calibration and the quality control.

One embodiment of the present invention has the advantage that the number of reference materials can be reduced by using the same reference materials in a second calibration as were used in the first calibration and quality control purposes without reducing the quality of the calibration and the quality control and yet retaining the independence between the calibration system and the quality control system. An improved calibration is obtained without using any supplementary reference materials.

A reference material may represent more than one parameter. This is an advantage if it is desired to determine several different parameters in one sample of test fluid and thus to calibrate or quality control more than one sensors simultaneously. If the reference material represents different parameters at various relevant levels it is possible to calibrate or quality control all sensors at one level in one operation. Many automatic analysers perform simultaneous multi analyte determination of a test fluid. One example is a blood analyser, such as the above-mentioned ABL™725 blood analyser.

The total range of the parameter levels of the reference materials should in the present method essentially cover the specified measuring range of the sensor. This is in order to ascertain that the measurements are reliable in that range.

Also, the distribution of the respective parameter levels of the various reference materials within the total range may influence the reliability of the quality control. If the correspondence determined in the calibration is used for conversion of a sensor response into a measured parameter value that lies outside the calibration range, the uncertainty of the determination will be greater the farther away from the calibration the measured or predetermined parameter value is.

If in a cycle the parameter levels of the reference materials used for performing the calibration upon which the quality control is based define a calibration range, and the parameter levels of all the reference materials used in the cycle define a total range, it is preferred that the calibration range is at least one fourth of the total range. It is particularly preferred that the calibration range is at least one third of the total range.

One embodiment of the present invention is particularly suitable for performing calibration and quality control of a sensor for determining a blood parameter, since it fulfils the legal requirements to calibration and quality control in the clinical field, is reliable and requires only limited maintenance from the operator and not at specific hours of the day. It will often be sufficient to renew the containers of reference fluid once or twice a month.

Further the containers may be provided in a cartridge and thus can be renewed without the operator having any prior knowledge as to the choice of containers or to the correct connection of the containers to the apparatus.

The method and apparatus of the present invention may be used in a number of different settings including, for example, an industrial laboratory, a clinic or hospital, a research center, and university. Besides the normal use of the apparatus in such settings, the method according to the present invention may also be practiced during the manufacture, testing, sale, and installation of the apparatus.

Thus, according to a preferred embodiment of the invention the parameter to be determined is a blood parameter, such as pH, $pCO_2$ and $pO_2$, electrolytes such as $Li^+$, $Na^+$, $K^+$, $Ca^{++}$, $Mg^{++}$, $Cl^-$, $HCO_3^-$ and $NH_4^+$, haemoglobin, haemoglobin, haemoglobin derivatives, Hct, or metabolic factors, such as bilirubin, glucose, lactate or creatinine.

According to another aspect of the present invention, an apparatus is provided for determining a parameter in a test fluid that includes: a sensor for obtaining a response to the parameter in the test fluid; reference materials representing at least two different parameter levels of the parameter; and a programmable device for controlling the functioning of the apparatus, wherein the programmable device performs calibration and quality control of the sensor for determining the parameter in the test fluid in which a calibration and quality control cycle is repeated, the cycle includes the steps of performing at least one calibration of the sensor using a reference material representing a parameter level of the parameter; performing at least one quality control of the sensor, as calibrated, using another reference material representing another parameter level of the parameter than in the calibration step, and repeating the above steps for at least two cycles, wherein in one cycle the reference material used in the quality control step was used in the calibration step of a previous cycle.

One embodiment of the present invention has the advantage that the number of reference materials may be reduced yet retaining the same precision and accuracy in the calibration and quality control and yet fulfilling the requirement that the reference material used in the quality control based upon a calibration is different from the reference material(s) used in the same calibration.

A reduction in the number of reference materials makes it possible to reduce the storage space for reference material. Inside the apparatus the storage requirement may also be reduced, thus reducing the size of the apparatus.

Further, the method according to one embodiment of the present invention provides a fully automated quality control routine, thus minimising the maintenance requirements and need for specially trained operators for operating such apparatuses. Also, the risk of human error is minimised.

The terms parameter, test fluid, sensor, and reference material are to be understood as having the same meanings as explained above.

The sensor response may include the energy formed in association with the change occurring at the sensing surface or the energy converted into electrical energy or electromagnetic radiant energy which is registerable by conventional converters.

The programmable device carrying out the functions and operations of certain aspects of the present embodiment may include, for example, a microprocessor or parallel processor, a memory bus, random access memory (RAM), and read only memory (ROM). The processor may be a general purpose digital processor which controls the operation of the programmable device. Using instructions retrieved from memory, the processor controls the reception and manipulation of input data and the output and display of data. However, those skilled in the art will appreciate that the method and system of the present invention may be advantageously implemented in a variety of hardware configurations.

The function and operation of the apparatus which the device may be programmed to control includes, for example, control of the means for exposing the sensor to test fluid and reference material and recording and processing of sensor responses. The processing of sensor responses may, for example, include determining a calibration correspondence on the basis of recorded sensor responses corresponding to calibration material(s), comparing a recorded sensor response corresponding to a quality control material with a calibration correspondence, and obtaining measured parameter values from recorded sensor responses on the basis of a determined calibration correspondence.

To process a sensor response of the sensor into a measured parameter value, the apparatus preferably comprises an operational amplifier for amplifying and converting the sensor response as well as an appropriate algorithm and software for executing the processing of the signal. The choice of an amplifier for amplifying the sensor response naturally depends on the nature of the sensor. The algorithm for converting the amplified sensor response into a measured parameter value may comprise the correspondence determined in the calibration and appropriate adjustments taking into account diverse systematic errors in the measuring method. Examples are given above.

The apparatus according to one embodiment of the present invention will in general also comprise means for exposing the sensor to the test fluid, means for exposing the sensor to the reference material and means for reporting a measured parameter value.

To expose the sensor to the test fluid, the apparatus may, for instance, comprise inlet means for introducing the test fluid into the apparatus. The inlet means may be designed to receive the outlet opening of a sample container such as a syringe or a capillary or a specially designed sample container.

The apparatus may further comprise an inlet probe for aspirating the sample of test fluid into the apparatus. Alternatively, the inlet may lead directly to a measuring chamber. The inlet or the inlet probe may be in fluid tight communication with a conduit. The conduit may comprise measuring chambers. It is preferably a tubing or a channel providing a fluid-tight path for transport of fluid through the conduit. The fluid may be transported through the conduit by means of a pump.

The sensor is exposed to the test fluid, either directly in the conduit or in a measuring chamber. The exposure of the sensor to the test fluid may be a direct physical contact between the sensing surface and the test fluid or it may be an indirect contact, the wall of the conduit or the measuring chamber separating the sensing surface from the test fluid. If optical sensing methods are employed, this part of the wall should be transparent to the type of radiation used.

The reference materials may be of the nature described above and may, for example, contain any of the parameters mentioned earlier. A total of two or three reference materials are preferred, but one or more further reference materials for calibrating the sensor may be included.

To expose the sensor to the reference material, the apparatus may include the same or similar components used to expose the sensor to the test fluid, as discussed above. It should however also include a mechanical device, which is capable of moving reference material from a storage location to a location providing operational communication between the sensor surface and the reference material. If the reference materials are fluid the device is preferably a pump. If they are solid the device is preferably a robot arm or similar device.

To report a measured parameter value, the apparatus may for example include a scale, a display, a printer, or a digital voice reporting the measured parameter value obtained from the processing means.

The apparatus may comprise more than one sensor. Preferably each sensor is specific towards one of the above-mentioned parameters.

The sensors may be miniaturized planar sensors. These may be located in a cassette for simultaneous renewal of all sensors.

The parts of such an apparatus being in contact with test fluid and/or reference fluid are often referred to as belonging to the wet section of the apparatus. This wet section may be an integral part of the apparatus or it may be provided in the form of a separate unit such as a cassette. The cassette may comprise several measuring chambers and/or sensors.

Preferably all the reference materials are located in a cartridge. Thus instead of changing one reference material at a time, two or more reference materials may be renewed in one operation. This provides a more user-friendly renewal of reference materials, particularly if the reference materials are fluids provided in containers. The cartridge may also contain a waste container into which the used reference materials and the used samples of test fluid are discarded.

When a parameter level of a test fluid is to be determined a sample of the test fluid is introduced into an apparatus as described above and the analysis of the sample is performed automatically. The reported measured parameter value is obtained from the apparatus.

The apparatus according to the present embodiment is preferably a blood analyser.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
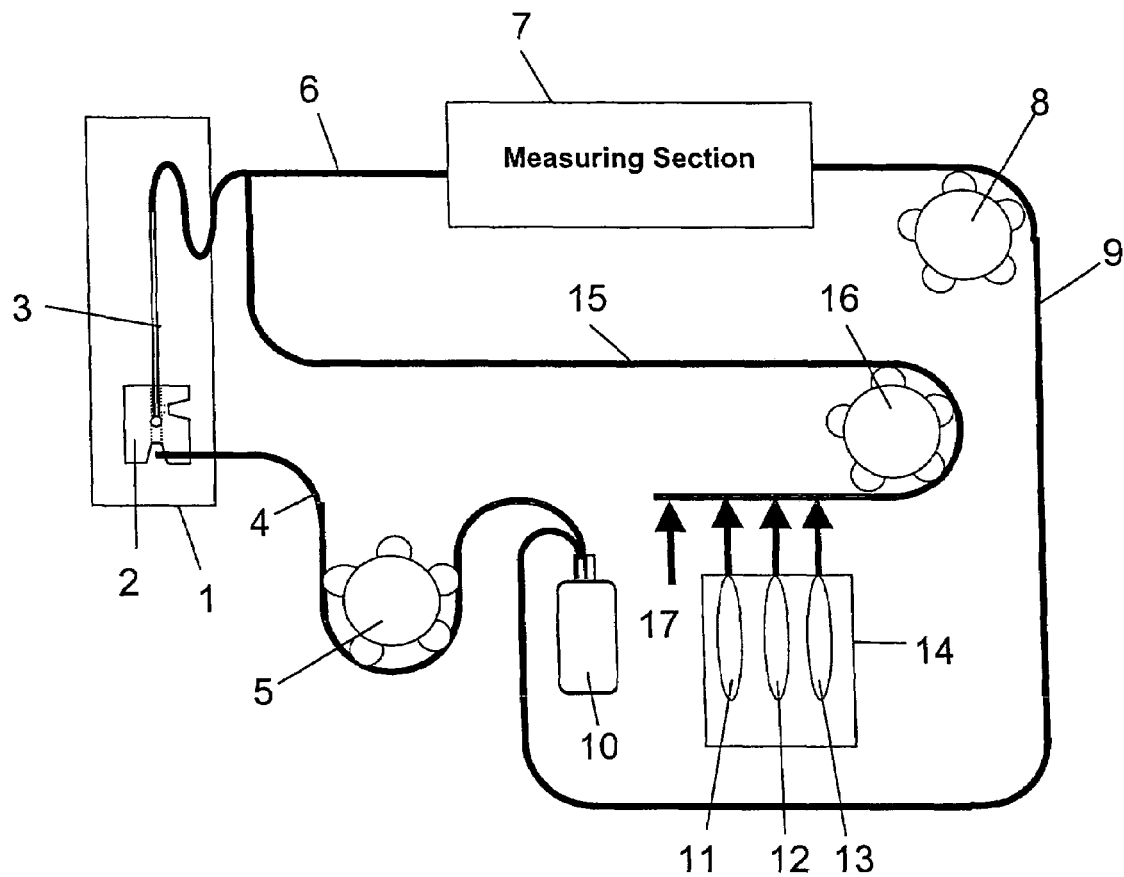
FIG. 1 is a schematic drawing of the modified wet section of an automatic blood analyser according to one embodiment of the present invention.

According to a preferred embodiment of the invention the method of performing calibration and quality control of a sensor is applied to a blood analyser having a wet section as shown in FIG. 1.

In FIG. 1 an inlet module 1 provides test fluid access to the apparatus. The inlet module 1 comprises an inlet gasket 2 provided with a cone for receiving the Luer of a syringe and a cone for receiving a capillary. A channel is leading from the cones through the gasket 2 to an inlet probe 3. If a syringe containing test fluid is connected to the inlet gasket 2, the inlet probe 3 may be displaced into the syringe and a sample of test fluid aspirated into the apparatus. The inlet gasket 2 is further provided with a tubing 4 and pump 5 for collecting any sample spills into a waste container 10.

The sample is transported through the tubing 6 to a measuring section 7 by means of pumps positioned after the measuring section, the pumps being represented by the pump 8. The measuring section 7 is thermostatically controlled at 37° C. The measuring section 7 comprises sensors selective towards pH, $CO_2$, $O_2$, Cl, Ca, Na, K, glucose, lactate sensors, a reference sensor, and an oxymetry module.

After analysis the sample is transported through the tubing 9 by means of the pump 8 to the waste container 10.

The wet section further comprises a liquid cartridge 14 containing reference fluid containers 11, 12 or 13, tubing 15, a pump 16, and an air inlet 17.

When a calibration or quality control measurement is performed, a sample of reference fluid is transported from one of the respective reference fluid containers 11, 12 or 13, contained in the liquid cartridge 14 through the tubing 15 to the measuring section 7 by means of the pumps 16 and 8. After analysis the sample is transported to the waste container 10 as described above.

After each measurement a rinsing procedure is performed. The measuring section 7 is flushed with one of the reference fluids 11, 12 or 13 further comprising components with rinsing action. The air inlet 17 is used for introducing air bubbles into the stream of calibration solution when a rinsing procedure is performed. This provides a better cleaning action.

In the following non-limiting example, reference fluids are prepared as described in U.S. Pat. No. 5,910,445. The compositions are as follows:

TABLE 1

Compositions of reference fluids.

| chemical species | Ref. 1 | Ref. 2 | Ref. 3 | Unit |
|---|---|---|---|---|
| MOPS | 51.9642 | 27.9425 | 37.5593 | mmol/kg $H_2O$ |
| NaOH | 32.8466 | 9.0839 | 30.1676 | mmol/kg $H_2O$ |
| NaCl | 104.5205 | 61.7754 | 142.1083 | mmol/kg $H_2O$ |
| KCl | 4.2818 | 7.5475 | 2.1564 | mmol/kg $H_2O$ |
| $CaCl_2$ | 0.9587 | 1.5985 | 0.3875 | mmol/kg $H_2O$ |
| $NaHCO_3$ | 11.7346 | 12.3584 | 9.4234 | mmol/kg $H_2O$ |
| glucose | 0.0 | 15.4784 | 7.2232 | mmol/kg $H_2O$ |
| Na-lactate | 0.0 | 9.6192 | 4.8096 | mmol/kg $H_2O$ |
| Na-sulforhodamin | 0.0 | 1.6705 | 2.5059 | mmol/kg $H_2O$ |

The above compositions provide reference fluids with predetermined parameter values for calibration purposes as given below in table 2:

TABLE 2

Predetermined parameter values (PPV) of reference fluids for calibration purposes.

| Parameter | Ref. 1 | Ref. 2 | Ref. 3 | Unit |
|---|---|---|---|---|
| pH | 7.200 | 6.800 | 7.600 | |
| $pCO_2$ | 30.0 | 70.0 | 10.0 | mmHg |
| $pO_2$ | 170.0 | 90.0 | 50.0 | mmHg |
| $cK^+$ | 4.0 | 7.0 | 2.0 | mmol/L |
| $cNa^+$ | 140.0 | 90.0 | 180.0 | mmol/IL |
| $cCa^{++}$ | 0.8 | 1.65 | 0.40 | mmol/L |
| $cCl^-$ | 100.0 | 65.0 | 130.0 | mmol/L |
| cGlu | 0 | 15 | 7 | mmol/L |
| cLac | 0 | 8 | 4 | mmol/L |
| tHb | 0 | 9 | 12 | mmol/L |

The acceptance ranges of these reference fluids for quality control purposes are as follows:

TABLE 3

Acceptance ranges (PPV) of reference fluids for quality control purposes.

| Parameter | Ref. 1 | Ref. 2 | Ref. 3 | Unit |
|---|---|---|---|---|
| pH | 7.163-7.203 | 6.785-6.825 | 7.560-7.600 | |
| $pCO_2$ | 26.4-32.4 | 61.8-71.8 | 8.8-12.8 | mmHg |
| $pO_2$ | 158-178 | 82-102 | 55-75 | mmHg |
| $cK^+$ | 3.3-3.9 | 6.0-6.6 | 1.7-2.3 | mmol/L |
| $cNa^+$ | 125-134 | 75-85 | 163-168 | mmol/IL |
| $cCa^{++}$ | 0.69-0.89 | 1.48-1.68 | 0.33-0.53 | mmol/L |
| $cCl^-$ | 90-102 | 61.0-73.0 | 120-132 | mmol/L |
| cGlu | 0-1 | 13.1-15.1 | 5.4-7.4 | mmol/L |
| cLac | 0-1 | 6.4-7.4 | 2.7-3.7 | mmol/L |
| tHb | 0-0.6 | 8.4-9.6 | 11.3-12.7 | mmol/L |

A first cycle of calibration and quality control is initialised by running an analysis of each of the three reference fluids Ref. 1, Ref. 2 and Ref 3.

The wet section including measuring chambers is flushed with reference fluid Ref. 1 in an amount corresponding to approximately twice the volume of the wet section. The wet section is filled again upon which sensor measurements are recorded every second for 30 seconds. This is a calibration measurement (Cal).

The above is repeated with Ref. 2.

Then the wet section is filled once with a sample of reference fluid Ref. 3 and sensor measurements are recorded every second for 30 seconds. The wet section is then flushed with reference fluid Ref. 3 in an amount corresponding to approximately the volume of the wet section. The wet section is filled again with Ref. 3, and sensor measurements are recorded every second for another 30 seconds. The first of the measurements is a quality control measurement (QC) and the second measurement is a calibration measurement (Cal).

After approximately eight hours the above cycle is repeated except that the double measurement is performed on Ref 2. After another eight hours the above cycle is repeated except that the double measurement is performed on Ref 1.

In the following, the example is explained only with regard to the parameter pH. However the results of the measurements of any of the other parameters may be processed similarly. The obtained measured parameter values of pH are:

TABLE 4

Measured parameter values of pH in cycle 1, 2 and 3.

| | Ref. 1 | Ref. 2 | Ref. 3 | Ref. 1 | Ref. 2 | Ref. 3 |
|---|---|---|---|---|---|---|
| | QC measurements | | | calibration measurements | | |
| Cycle 1 | — | — | 7.575 | 7.195 | 6.804 | 7.602 |
| Cycle 2 | — | 6.805 | — | 7.200 | 6.800 | 7.601 |
| Cycle 3 | 7.189 | — | — | 7.205 | 6.798 | 7.605 |

In cycle 1 a first calibration is obtained by estimating the correspondence between the predetermined parameter values (PPV) and the measured parameter values (MPV) of Ref. 1 and Ref. 2. The measured QC parameter level (MPV) of Ref. 3, which is obtained using the first calibration, is then compared to the assigned parameter level (PPV) with acceptance limits. This is depicted in FIG. 2.

Figure 2:
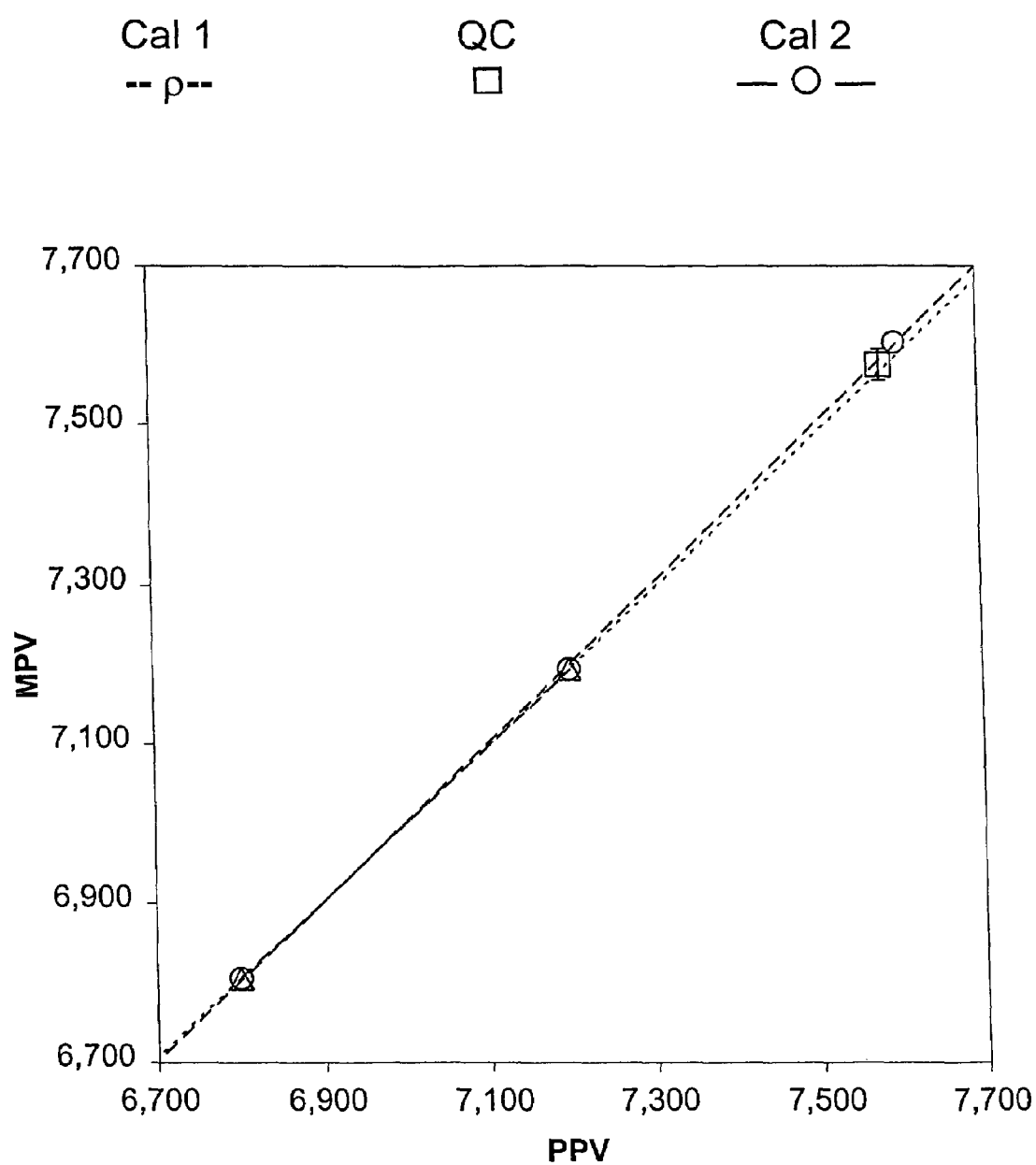
FIG. 2 is a chart representing the first calibration curve and corresponding quality control as well as the second calibration curve for a pH sensor.

As shown in FIG. 2 the QC parameter level of pH is within the acceptance limits and the quality control is accepted.

Subsequently, a second calibration is obtained based on all three calibration measurements, which second calibration may be used in determining measured parameter values of a test fluid. This second calibration curve is also depicted in FIG. 2.

The results of the two other cycles may be processed similarly. All quality controls fall within the acceptance limits as can be deduced from table 4.

If three reference materials are used, the full routine of calibration and quality control comprises at least three cycles. The reference materials may be combined in a number of ways. A few combinations are exemplified below. The cycles A, B and C may be performed in any order.

TABLE 5

In all cycles the quality control is based on a two-point calibration.

| Cycle number | Ref. 1 | Ref. 2 | Ref. 3 |
|---|---|---|---|
| A | QC | cal | cal |
| B | cal | cal | QC |
| C | cal | QC | cal |

TABLE 6

Three reference materials are used, but in every cycle one reference material is a "dummy".

| Cycle number | Ref. 1 | Ref. 2 | Ref. 3 |
|---|---|---|---|
| A | — | QC | cal |
| B | cal | — | QC |
| C | QC | cal | — |

TABLE 7

Quality control is performed in two points in every cycle, and calibration in one point.

| Cycle number | Ref. 1 | Ref. 2 | Ref. 3 |
|---|---|---|---|
| A | QC | QC | cal |
| B | cal | QC | QC |
| C | QC | cal | QC |

TABLE 8

In some areas of the total range it is preferred that the quality control is based on a two-point calibration, in others a one point calibration is sufficient.

| Cycle number | Ref. 1 | Ref. 2 | Ref. 3 |
|---|---|---|---|
| A | cal | QC | cal |
| B | cal | — | QC |
| C | cal | cal | — |

If more than three reference materials are used in the method, a further calibration point may be introduced and/or a second quality control may be performed. Optionally, some cycles of a full routine of calibration and quality control may include the further reference material(s) whereas they are left out in other cycles.

If four reference materials are used, the full routine of calibration and quality control comprises at least four cycles. The reference materials may be combined in a number of ways. A few combinations are exemplified below. The cycles A, B, C and D may be performed in any order.

TABLE 9

In all cycles a three-point calibration is performed.

| Cycle number | Ref. 1 | Ref. 2 | Ref. 3 | Ref. 4 |
|---|---|---|---|---|
| A | cal | cal | cal | QC |
| B | cal | cal | QC | cal |
| C | cal | QC | cal | cal |
| D | QC | cal | cal | cal |

TABLE 10

Four reference materials are used, but in every cycle one reference material is a "dummy".

| Cycle number | Ref. 1 | Ref. 2 | Ref. 3 | Ref. 4 |
|---|---|---|---|---|
| A | — | QC | cal | cal |
| B | cal | — | QC | cal |
| C | cal | cal | — | QC |
| D | QC | cal | cal | — |

TABLE 11

Quality control is performed at two levels in every cycle.

| Cycle number | Ref. 1 | Ref. 2 | Ref. 3 | Ref. 4 |
|---|---|---|---|---|
| A | QC | QC | cal | cal |
| B | cal | QC | QC | cal |
| C | cal | cal | QC | QC |
| D | QC | cal | cal | QC |

TABLE 12

In some areas of the total range it is preferred that a three-point calibration is performed, in others a two-point calibration is sufficient.

| Cycle number | Ref. 1 | Ref. 2 | Ref. 3 | Ref. 4 |
|---|---|---|---|---|
| A | cal | QC | cal | cal |
| B | cal | — | QC | cal |
| C | cal | cal | — | QC |
| D | QC | cal | cal | — |

It will be apparent to those skilled in the art that various modifications and variations can be made in the method and system of the present invention without departing from the spirit or scope of the invention. Thus, it is intended that the present invention cover the modifications and variations of this invention provided they come within the scope of the appended claims and their equivalents.

The invention claimed is:

1. A method of performing calibration and quality control of a sensor for determining a parameter in a test fluid in which a calibration and quality control cycle is repeated, the cycle comprising the steps of:

performing at least one calibration of the sensor using a reference material representing a parameter level of the parameter;

performing at least one quality control of the sensor, as calibrated, using another reference material representing another parameter level of the parameter than in the calibration step; and repeating the above steps for at least two cycles, wherein in one cycle the reference material used in the quality control step was used in the calibration step of another cycle.

2. The method according to claim 1, wherein two or more reference materials representing different parameter levels of the parameter are used in the calibration step.

3. The method according to claim 2, wherein in the cycle
the parameter levels of the reference materials used for performing the calibration upon which the quality control is based define a calibration range;
the parameter levels of all the reference materials used in said cycle define a total range; and
said calibration range is at least one fourth of said total range.

4. The method according to claim 2, wherein in the cycle
the parameter levels of the reference materials used for performing the calibration upon which the quality control is based define a calibration range;
the parameter levels of all the reference materials used in said cycle define a total range; and
said calibration range is at least one third of said total range.

5. The method according to claim 1, wherein the cycle is repeated until each of the reference materials have been used at least once for quality control of the sensor.

6. The method according to claim 1, wherein in the cycle the calibration performed in the calibration step is a first calibration and that the cycle further comprises the step of
performing a second calibration of the sensor using the same reference materials as were used in the first calibration step and in the quality control step.

7. The method according to claim 6, wherein in the cycle
sensor responses are obtained to the reference materials used in the first calibration step and the quality control step;
a further sensor response is obtained to the reference material used in the quality control step; and
the second calibration is based on the sensor responses obtained in the first calibration step and on the further sensor response obtained.

8. The method according to claim 6, wherein in the cycle
sensor responses are obtained to the reference materials used in the first calibration step and the quality control step; and
the second calibration is based on the sensor responses obtained in the first calibration step and the quality control step.

9. The method according to claim 1, wherein the parameter is a blood parameter.

10. The method according to claim 1, wherein the reference materials are fluids held in sealed containers.

11. A method of performing calibration and quality control of a sensor for determining a parameter in a test fluid comprising the steps of:

performing a first calibration of the sensor using a reference material representing a parameter level of the parameter;

performing a quality control of the sensor, as calibrated, using another reference material representing another parameter level of the parameter than in the calibration step; and performing a second calibration of the sensor using the same reference materials as were used in the steps of performing the first calibration and the quality control.

12. The method according to claim 11, wherein two or more reference materials representing different parameter levels of the parameter are used in the calibration step.

13. The method according to claim 12, wherein
the parameter levels of the reference materials used for performing the calibration upon which the quality control is based define a calibration range;
the parameter levels of all the reference materials used define a total range; and
said calibration range is at least one fourth of said total range.

14. The method according to claim 11, wherein
sensor responses are obtained to the reference materials used in the first calibration step and the quality control step;
a further sensor response is obtained to the reference material used in the quality control step; and
the second calibration is based on the sensor responses obtained in the first calibration step and on the further sensor response obtained.

15. The method according to claim 11, wherein
sensor responses are obtained to the reference materials used in the first calibration step and the quality control step; and
the second calibration is based on the sensor responses obtained in the first calibration step and the quality control step.

16. The method according to claim 11, wherein the parameter is a blood parameter.

17. The method according to claim 11, wherein the reference materials are fluids held in sealed containers.

18. An apparatus for determining a parameter in a test fluid comprising
a sensor sensitive to the parameter in the test fluid and providing a sensor response;
reference materials representing at least two different parameter levels of the parameter; and
a programmable device for controlling the functioning of the apparatus,
wherein the programmable device is programmed to control the perfpormance of calibration and quality control of the sensor in which a calibration and quality control cycle is repeated, the cycle comprising
performance of at least one calibration of the sensor using a reference material representing a parameter level of the parameter;
performance of at least one quality control of the sensor, as calibrated, using another reference material representing another parameter level of the parameter than in the calibration; and
subsequent performance of the above calibration and quality control for at least two cycles,
wherein in one cycle the reference material used in the quality control was used in the calibration of a previous cycle.

19. The apparatus according to claim 18 further comprising
means for exposing the sensor to a portion of the test fluid;
means for exposing the sensor to the reference materials for the parameter and obtaining a response; and
means for reporting a measured parameter value, and wherein the programmable device comprises means for determining the measured parameter value.

20. The apparatus according to claim 18, wherein the apparatus comprises reference materials representing at least three different parameter levels of the parameter.

21. The apparatus according to claim 18, wherein at least two reference materials are located in one cartridge.

22. The apparatus according to claim 18, wherein the sensor is a miniaturized planar sensor.

23. The apparatus according to claim 18, wherein the sensor is located in a measuring chamber forming an integral part of the apparatus.

24. The apparatus according to claim 18, wherein the sensor is located in a removable cassette.

25. The apparatus according to claim 18, wherein the apparatus is a blood analyzer.

26. A method of performing calibration and quality control of a sensor for determining a parameter in a test fluid comprising:
performing multiple calibration and quality control cycles comprising:
(a) performing a calibration of the sensor; and
(b) performing a quality control of the sensor as calibrated,
wherein in at least one of the calibration and quality control cycles, the step (a) of performing a calibration includes obtaining a sensor response corresponding to a first reference material which represents a first parameter level of the parameter, and the step (b) of performing a quality control includes obtaining a sensor response corresponding to a second reference material which represents a second parameter level of the parameter, wherein the first parameter level and the second parameter level differ, and
wherein in at least another of the calibration and quality control cycles, the step (b) of performing a quality control includes obtaining a sensor response corresponding to the first reference material.

27. The method according to claim 26, wherein in the at least one calibration and quality control cycle, the step (a) further includes obtaining a sensor response corresponding to a third reference material, wherein said first reference material and said third reference material represent different parameter levels of the parameter.

28. The method according to claim 27, wherein in the at least one calibration and quality control cycle:
the step (a) comprises obtaining sensor responses corresponding to two or more reference materials, the reference materials representing different parameter levels of the parameter and the parameter levels defining a calibration range;
the parameter levels of all the reference materials used in said cycle define a total range; and
said calibration range is at least one fourth of said total range.

29. The method according to claim 27, wherein in the at least one calibration and quality control cycle:
the step (a) comprises obtaining sensor responses corresponding to two or more reference materials, the reference materials representing different parameter levels of the parameter and the parameter levels defining a calibration range;
the parameter levels of all the reference materials used in said cycle define a total range; and
said calibration range is at least one third of said total range.

30. The method according to claim 26, wherein in the at least one calibration and quality control cycle, the step (a) further includes obtaining multiple sensor responses corresponding to multiple reference materials, wherein said first reference material and said multiple reference materials represent different parameter levels of the parameter.

31. The method according to claim 26, wherein in the multiple calibration and quality control cycles, each of the reference materials is used at least once in the steps (b) of performing a quality control of the sensor as calibrated.

32. The method according to claim 26, wherein in the at least another calibration and quality control cycle, the step (a) includes obtaining a sensor response corresponding to one or more reference materials, wherein said one or more reference materials and said first reference material each represent different parameter levels of the parameter.

33. The method according to claim 26, wherein the at least one calibration and quality control cycle further comprises:

(c) performing a second calibration of the sensor using at least one of the sensor responses corresponding to the first reference material and the second reference material.

34. The method according to claim 26, wherein the at least one calibration and quality control cycle further comprises:

(c) performing a second calibration of the sensor including obtaining a second sensor response corresponding to the second reference material and using at least the sensor response corresponding to the first reference material and the second sensor response corresponding to the second reference material to determine a calibration relationship of the sensor.

35. The method according to claim 26, wherein the parameter is a blood parameter.

* * * * *